(12) United States Patent
Cocchia et al.

(10) Patent No.: US 6,224,545 B1
(45) Date of Patent: May 1, 2001

(54) SURGICAL RETRACTOR AND METHOD FOR USE

(75) Inventors: Pasquale Cocchia, Rever, MA (US); Lester Cohen, New York, NY (US)

(73) Assignee: Core Surgical, Inc., New York, NY (US)

( * ) Notice: Subject to any disclaimer, the term of this patent is extended or adjusted under 35 U.S.C. 154(b) by 0 days.

(21) Appl. No.: 09/359,317

(22) Filed: Jul. 23, 1999

Related U.S. Application Data

(60) Provisional application No. 60/093,992, filed on Jul. 24, 1998.

(51) Int. Cl.$^7$ .................................................. A61B 1/32
(52) U.S. Cl. ............................................................. 600/233
(58) Field of Search .................................. 600/227, 231, 600/232, 233, 201

(56) References Cited

U.S. PATENT DOCUMENTS

| | | | |
|---|---|---|---|
| 475,975 | * | 5/1892 | Clough ............................ 600/233 X |
| 3,724,449 | * | 4/1973 | Gauthier .......................... 600/233 X |
| 4,852,552 | | 8/1989 | Chaux . |
| 4,924,857 | * | 5/1990 | Mahmoodian .................... 600/231 X |
| 5,503,617 | * | 4/1996 | Jako .................................... 600/201 |
| 5,813,978 | * | 9/1998 | Jako .................................... 600/201 |

FOREIGN PATENT DOCUMENTS

| 2462643 | * | 9/1977 | (DE) ..................................... 600/233 |
|---|---|---|---|
| 9320741 | | 10/1993 | (WO) . |

* cited by examiner

Primary Examiner—Jeffrey A. Smith
(74) Attorney, Agent, or Firm—Stevens, Davis, Miller & Mosher, LLP

(57) ABSTRACT

A surgical retractor apparatus comprising a U-shaped thread assembly slidably engaged with a U-shaped rack. A rotatable threaded rod connects the U-shaped rack and the U-shaped thread assembly. A first swivel having a first blade mount is rotatably connected to the U-shaped rack and a second swivel having a second blade mount is rotatably attached to the thread assembly. A first blade is mounted in the first blade mount and a second blade is mounted in the second blade mount. The swivels have respective threaded screws to adjust the angle of each blade relative to a longitudinal plane passing through the U-shaped rack.

17 Claims, 16 Drawing Sheets

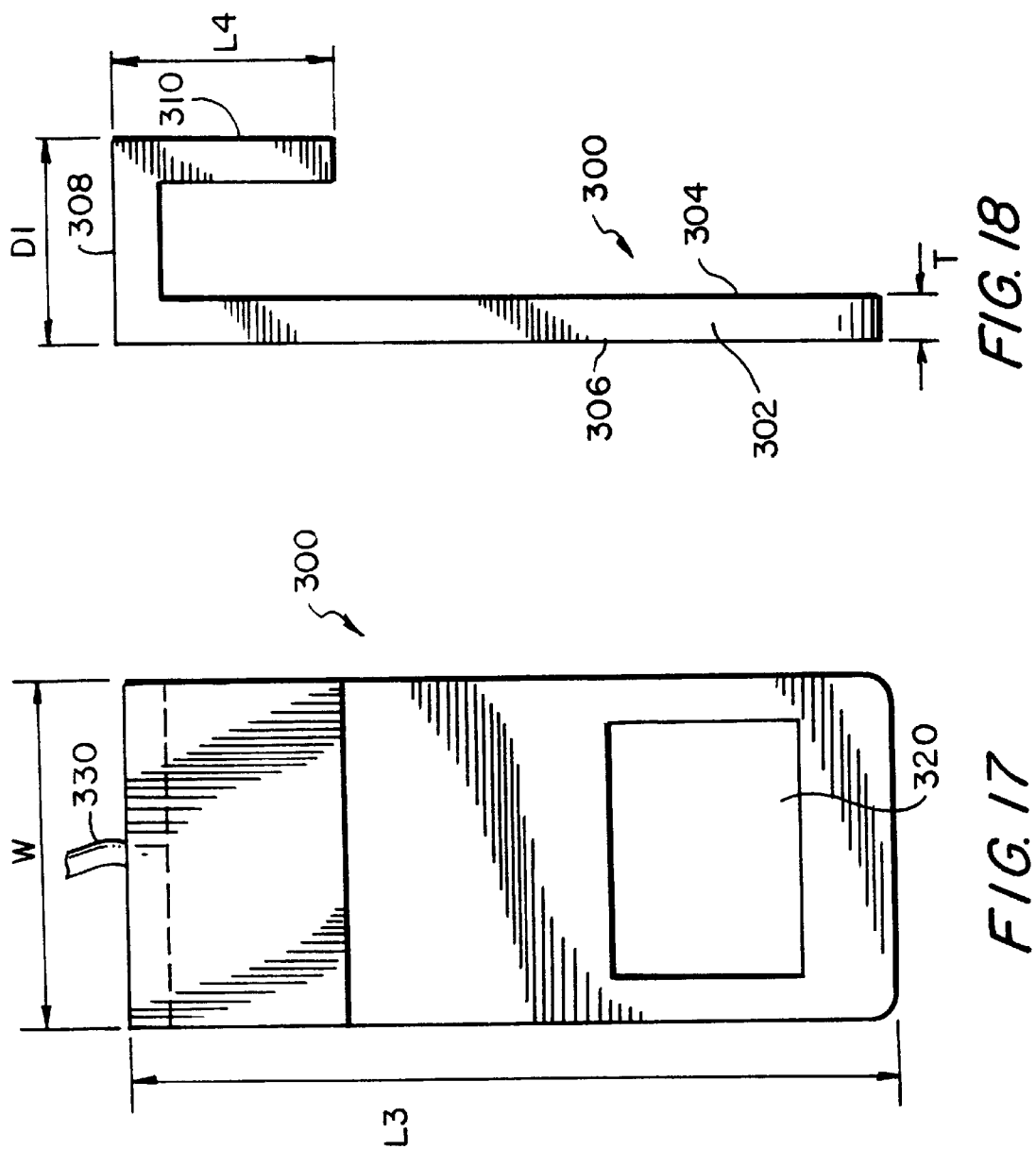

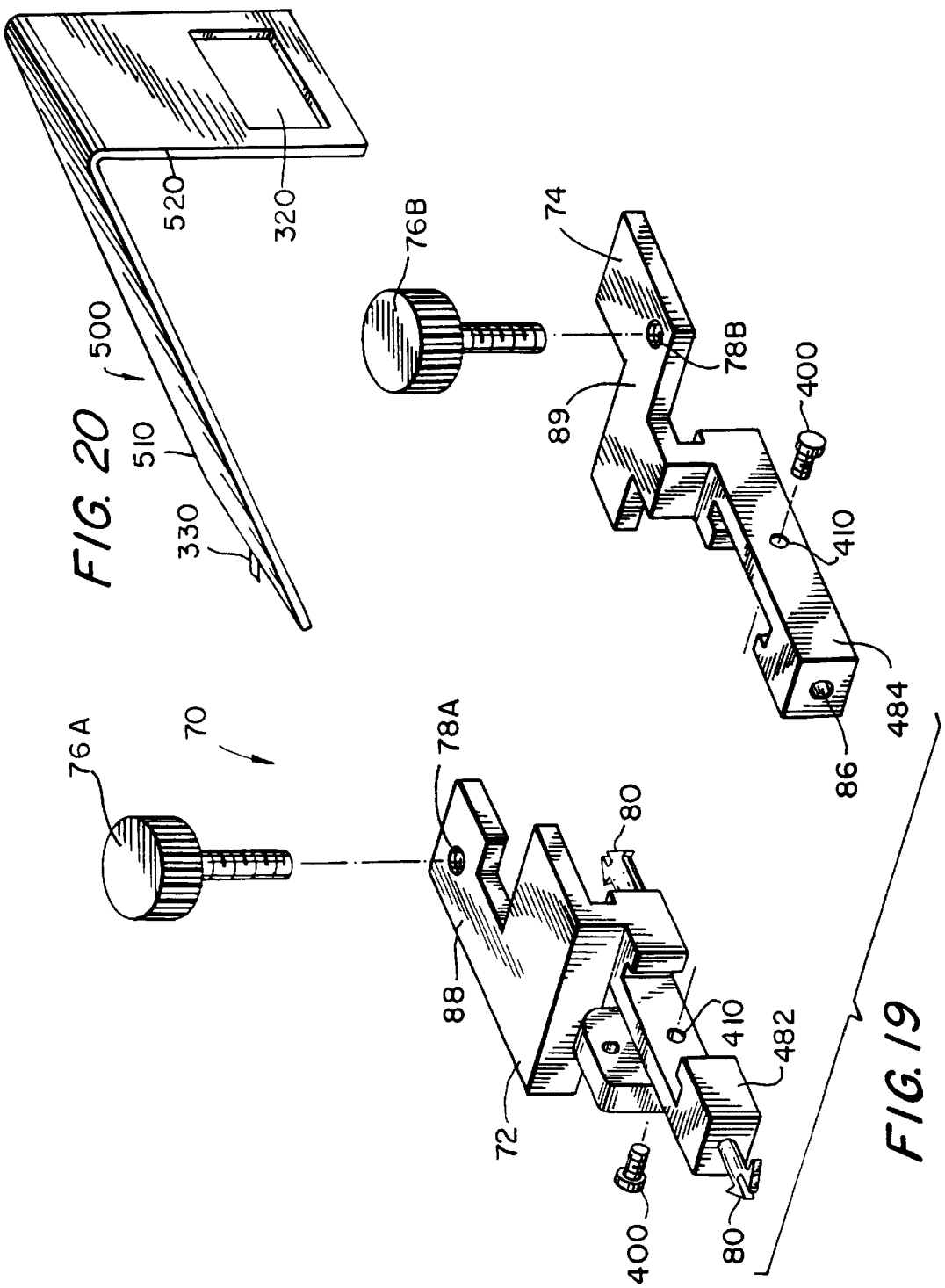

SURGICAL RETRACTOR AND METHOD FOR USE

This application claims priority from U.S. Provisional Patent Application No. 60/093,992, filed Jul. 24, 1998.

BACKGROUND OF THE INVENTION

1. Field of the Invention

The present invention relates to a surgical retractor for permitting a wide variety of surgeries through an operating window. More particularly, the retractor permits surgery through a small outer incision, i.e., outer operating window, while providing a field of operation within the patient's body, i.e., inner operating window, which is larger than the outer operating window.

2. Background Discussion

In many types of surgery it is necessary to make an incision in a patient through the patient's skin and underlying tissues to permit operating on internal organs, etc. of that patient. Thus the incision creates an opening through the epidermis, dermis, subcutaneous tissue (including fat cells), fascia (covering muscle), and muscle. In some cases, e.g., coronary by-pass, the incision must also cut through hard body tissue, i.e., sternum. A retractor is often needed to keep the tissues at either side of the incision sufficiently apart to keep open an operating window through which the surgery is performed. For example, sternal retractors are necessary instruments for performing coronary bypass surgery. See for example, U.S. Pat. No. 4,852,552 to Chaux, incorporated herein by reference. Retractors generally keep the operating window open by pushing the two opposed sides of the incision away from each other. Some retractors for endoscopic surgery are also provided with a fiberoptic mechanism to light the operating area. A retractor with a fiberoptic mechanism is disclosed by U.S. Pat. No. 5,503,617 to Jako. U.S. Pat. No. 5,503,617 to Jako asserts that its retractor has lower and upper blades wherein the angle of the lower blade relative to its lower blade mount and the angle of the upper blade relative to its upper blade mount can be adjusted independently. However, this device is somewhat complex.

Although a wide variety of surgical retractors are known, it would be advantageous to provide a surgical retractor which is easier to use than those commercially available, highly reliable, disposable, and more economical. It would also be advantageous to provide a surgical retractor which economically permits an internal operating window area which is larger than its external operating window.

SUMMARY OF THE INVENTION

It is an object of the present invention to provide a surgical retractor which, in a easy to use economical fashion, provides for an internal operating window of much greater area than an external operating window.

It is another object of the present invention to provide a method of surgery employing the surgical retractor of the present invention.

The apparatus of the present invention is a surgical retractor comprising a U-shaped rack having a first leg, a second leg and a rack crosspiece. The first leg and second leg extend from respective ends of the rack crosspiece and each leg defines a respective transverse slot having open sides. The rack crosspiece defines first and second receiving holes respectively longitudinally aligned with, and in communication with, one of the transverse slots. The surgical retractor also comprises a U-shaped thread assembly comprising a thread assembly crosspiece having traveler rods attached at or adjacent to opposed ends of the thread assembly crosspiece. A threaded rod is rotatably attached to the thread assembly crosspiece, the threaded rod being substantially parallel to the traveler rods and located between the traveler rods. The threaded rod has opposed first and second ends and is connected to the rack by a threaded receiving opening at the rack crosspiece. Each of the traveler rods is slidably connected to a respective one of the legs of the rack assembly by passing through a respective one of the receiving openings into a respective one of the slots.

A first blade and a second blade are also included. The first blade has a sidewall opposed to a sidewall of the second blade. A swivel assembly comprising a first swivel having a first blade mount is rotatably connected to the U-shaped rack opposite the rack crosspiece. A second swivel having a second blade mount is rotatably attached to the ends of the travelers opposite the thread assembly crosspiece. The first swivel comprises a first swivel arm having at least one threaded hole for passing at least one respective threaded screw therethrough. The at least one threaded screw of the first swivel contacts a surface of one of the legs of the rack to adjust an angle of the first blade relative to the legs of the rack. The second swivel has a second arm having at least one threaded hole for passing at least one respective threaded screw therethrough. The at least one threaded screw of the second swivel contacts a surface of the rack to adjust an angle of the second blade relative to the legs of the rack. The blades have respective proximal ends and distal ends. The proximal ends are attached to the respective blade mounts. The distal ends are distal to the blade mounts. By the unique, yet simple, structure of the present invention, the position of the blades is adjustable such that the blade distal ends can be further apart from each other than are the blade proximal ends. This achieves an internal operating window having an area larger than that of its external operating window.

The device may be made entirely of stainless steel or titanium. However, typically at least the blades are made of plastic such as polyurethane, polystyrene, polycarbonate, polyacrylate, polyethylene, or polypropylene. The polymers may be reinforced with conventional reinforcing agents such as natural or synthetic fibers, e.g., nylon, or carbon black. Preferably, the majority of the parts of the apparatus of the present invention are made of plastic to facilitate using the present retractor as a disposable retractor. Thus, preferably, parts such as the U-shaped racks, U-shaped thread assembly crosspiece, first swivel, second swivel and blades are made of plastic.

A disposable retractor is advantageous to minimize risks of transmitting infection from one surgical patient to another and ensures that a new reliable device is used for every surgery.

BRIEF DESCRIPTION OF THE DRAWINGS

The following briefly describes the drawings in which like elements are labeled by like numbers.

FIG. 17 shows a front view of a side blade of the present invention.

FIG. 18 shows a side view of a side blade of the present invention.

FIG. 19 is a perspective view of the swivel assembly of FIG. 6 modified to include thumbscrews to further hold blades in place.

FIG. 20 is a perspective view of a hand held retractor that may be used with the retractor of the present invention.

DETAILED DESCRIPTION OF THE PREFERRED EMBODIMENTS

Figure 1:
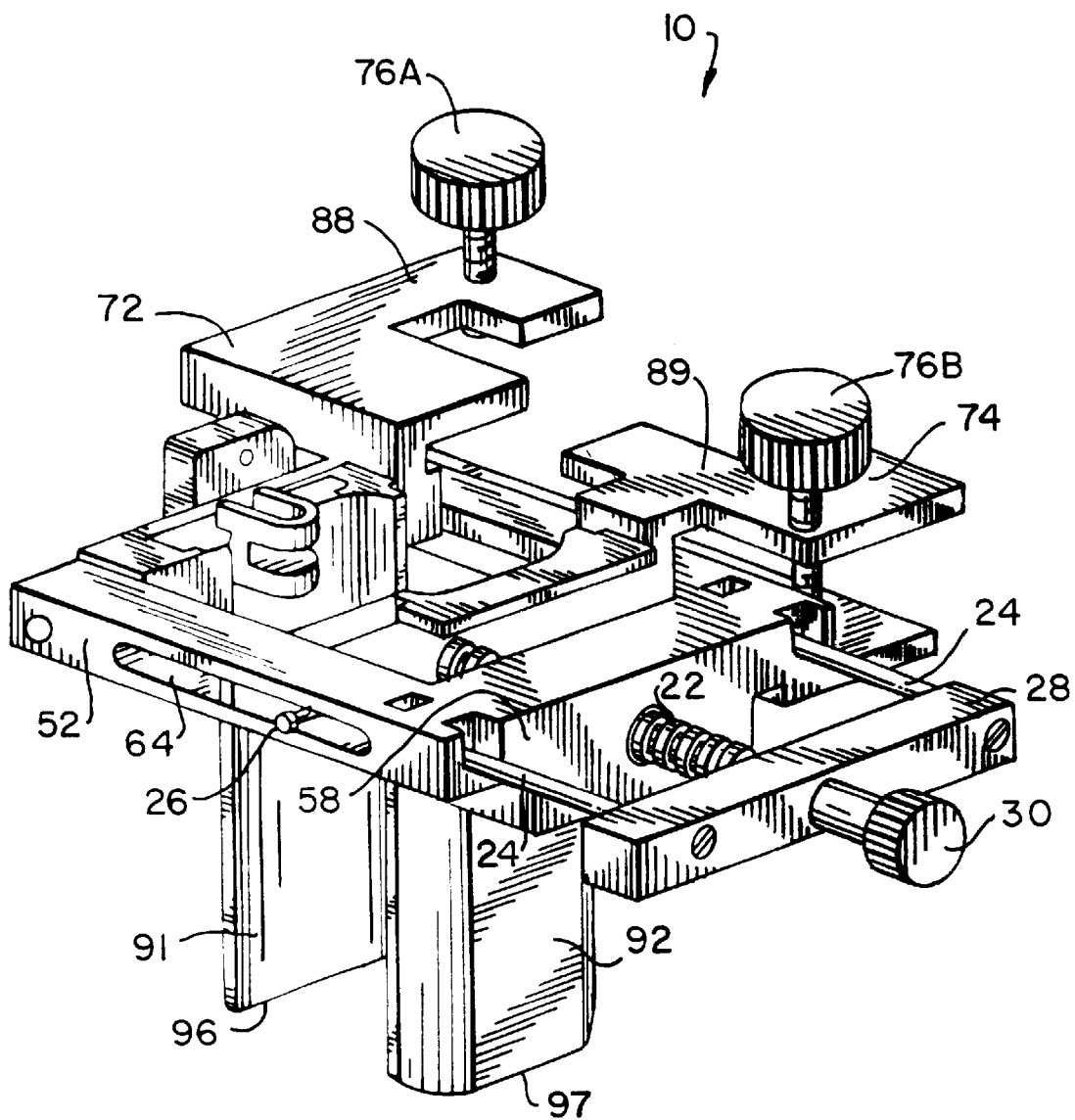
FIG. 1 is a perspective view of a first embodiment of a surgical retractor of the present invention.
Figure 2:
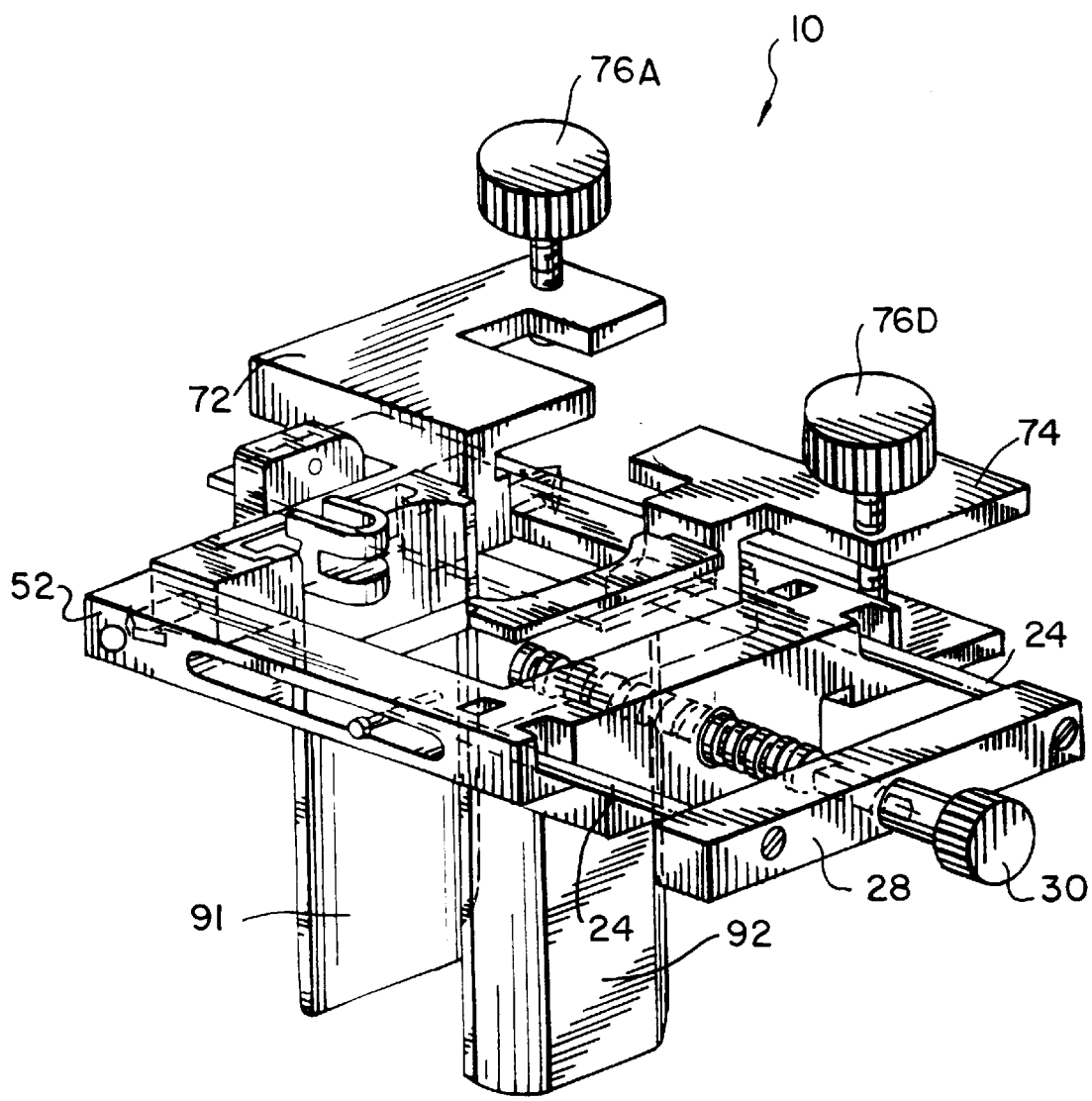
FIG. 2 is a view of the embodiment of FIG. 1 drawn to show internal parts of the embodiment.
Figure 3:
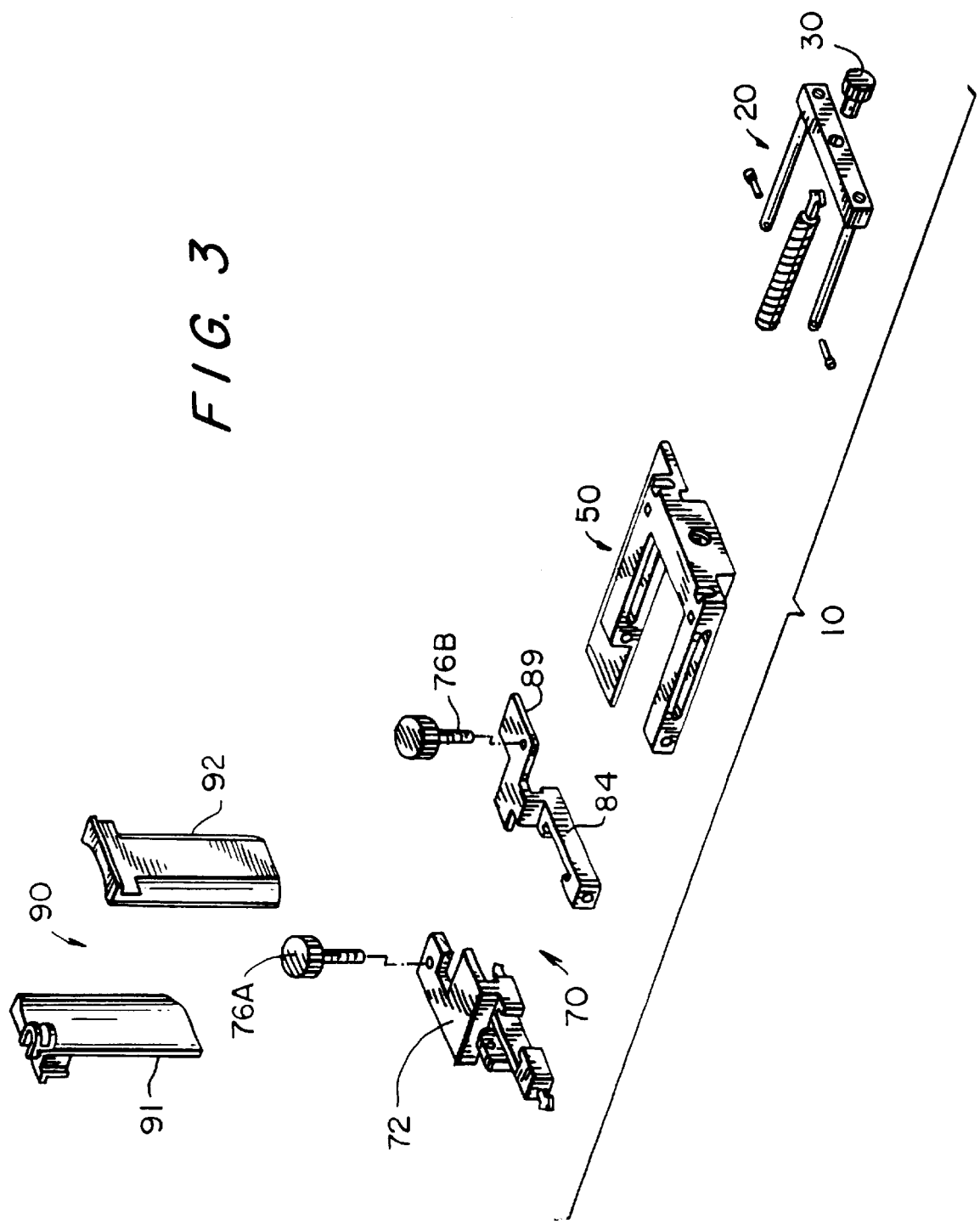
FIG. 3 is an exploded view of the embodiment of FIG. 1.

FIG. 1 shows a first embodiment of the assembled surgical retractor 10 of the present invention. As shown in FIG. 3, the surgical retractor 10 has a number of parts designed to fit together to provide smooth and efficient operation in the surgery room. The surgical retractor 10 comprises a thread assembly 20, a rack assembly 50, a swivel assembly 70, and removable blade assembly 90.

Figure 5:
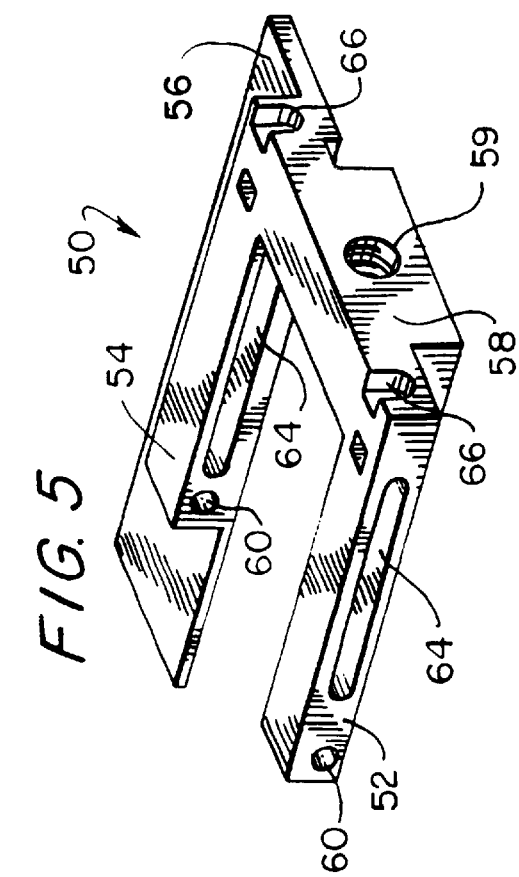
FIG. 5 is a perspective view of a rack assembly of the embodiment of FIG. 1.

As shown in FIG. 5, the rack assembly 50 is a U-shaped rack having a first leg 52, a second leg 54 and a rack crosspiece 58. The first leg 52 and second leg 54 extend from respective ends of the rack crosspiece 58. Each leg 52, 54 defines a respective elongate transverse slot 64 having open sides. The rack crosspiece 58 defines first and second receiving holes 66 aligned with the longitudinal axis of, and in communication with, one of the transverse slots 64. The rack assembly 50 also has openings 60 and a substantially planer platform 56 extending from the second leg 54. The rack crosspiece 58 also defines a threaded receiving opening 59, discussed in more detail below.

Figure 4:
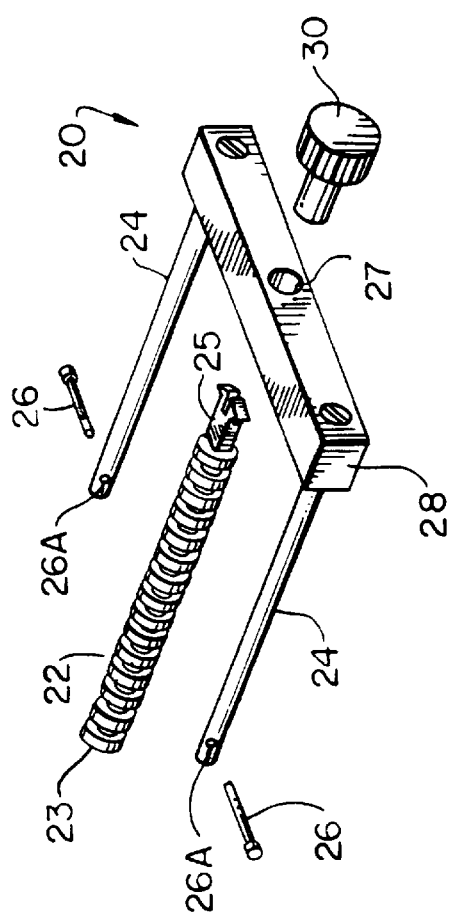
FIG. 4 is a view of a thread assembly of the embodiment of FIG. 1.

As shown by FIG. 1, the U-shaped thread assembly 20 slidably engages the rack assembly 50. As shown by FIG. 4, the U-shaped thread assembly 20 comprises a thread assembly crosspiece 28 having traveler rods 24 attached at or adjacent to opposed ends of the thread assembly crosspiece 28. A threaded rod 22 is rotatably attached to a midpoint of the thread assembly crosspiece 28. The threaded rod 22 is substantially parallel to the traveler rods 24 and is located between the traveler rods 24.

The threaded rod 22 has a first end 23 and a second end 25. Second end 25 passes through an opening 27 through the crosspiece 28 and interlocks with a knob 30. Knob 30 is a knurled knob rod to permit easy gripping for turning by the surgeon. Thus, the end 25 and knob 30 interlock so that turning knob 30 directly turns the threaded rod 22 to adjust the spacing between a proximal end 94 of first blade 91 and a proximal end 95 of second blade 92. As defined in this specification, proximal end 94 is proximal to a first blade mount 82 of the swivel assembly 70. Proximal end 95 is proximal to a second blade mount 84 of the swivel assembly 70. The blades 91, 92 also have distal ends 96, 97, which are distal to respective blade mounts 82, 84.

The blades 91, 92 are typically inserted into the respective blade mounts 82, 84 when the blade mounts 82, 84 are together such that the retractor 10 is in a closed position.

An element that is moved in place to overhang or otherwise contact the proximal ends 94, 95, respectively, may be provided. This element assists in holding the blades 91, 92 in the blade mounts 82, 84 as the blades 91, 92 are inserted into the patient. FIG. 19 shows an embodiment employing such an element. As shown in FIG. 19, thumbscrews 400 are provided to pass through threaded holes 410 of blade mounts 482, 484 to contact the respective blades 91, 92 and assist in holding the blades 91, 92 in place. Mounts 482, 484 otherwise are employed and configured as are mounts 82, 84.

The threaded rod 22 is slidably connected to the rack assembly 50 by the threaded receiving opening 59 at the rack crosspiece 58. Each traveler rod 24 is slidably connected to a respective one of the legs 52, 54 of the rack assembly 50 by passing through a respective one of the receiving openings 66 into a respective one of the slots 64. As shown by FIGS. 1, 4 and 5, the traveler rods 24 are attached within the legs 52, 54 by pins 26 which respectively pass through the slots 64 and attach to respective traveler rods 24 at rod side openings 26a.

Figure 7:
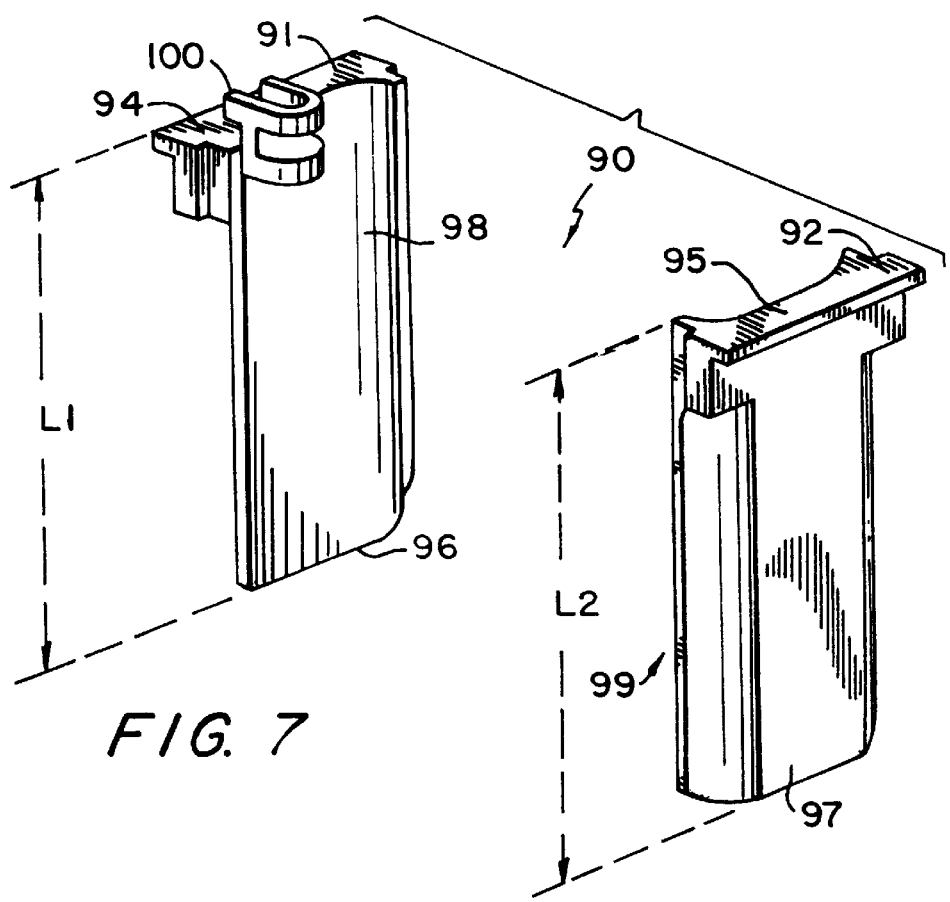
FIG. 7 is a perspective view of the blade assembly, comprising a first and second blade, of the embodiment of FIG. 1.
Figure 8:
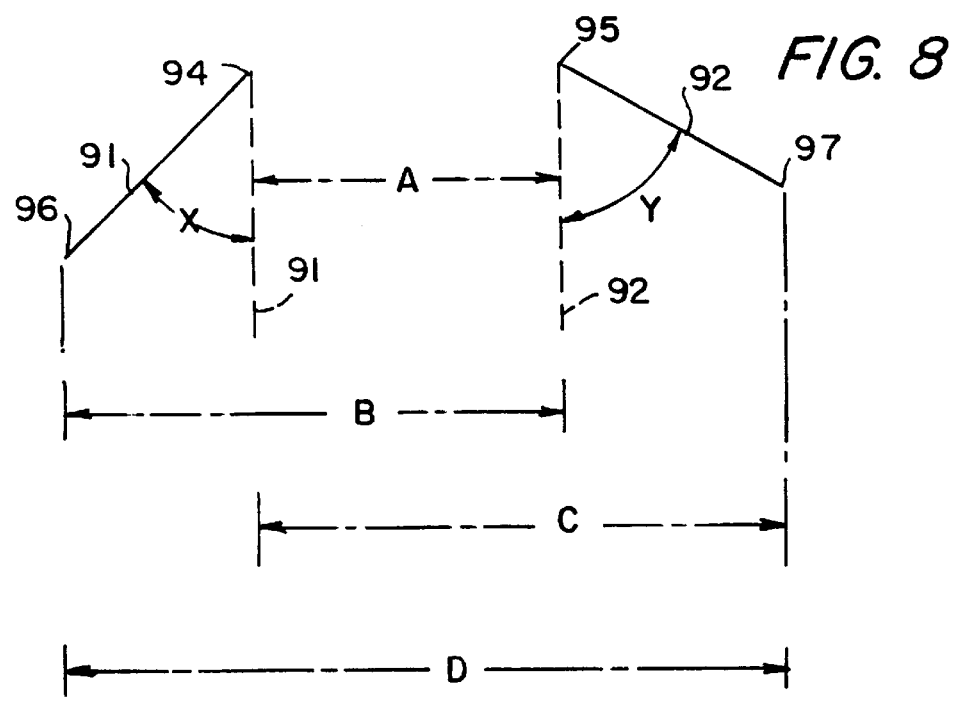
FIG. 8 is a schematic view of the blade assembly, comprising a first and second blade, of the embodiment of FIG. 1.

As shown by FIG. 7, the blade assembly 90 comprises first blade 91 and second blade 92. The blades 91, 92 have respective proximal ends 94, 95, distal ends 96, 97 and opposed sidewalls 98, 99. The blades 90, 91 are typically also provided with a conduit 100 for holding a fiberoptic cable (FIG. 7 shows one of the conduits 100). The blades 91, 92 are interchangeable, that is, they may be easily removed from the retractor 10 to be exchanged for other blades of differing compositions or lengths. In use, the blades 91, 92 may be of the same or different lengths. Lengths of the first and second blades 91, 92 are indicated on FIG. 8 by lengths L1, L2, respectively.

Preferably, the blades 91, 92 are made of a disposable material such as a sturdy surgically acceptable polymer. Typical suitable polymers are thermoplastic or thermoset resins such as polyvinylchloride, acetal resin (e.g., DELRIN available from DuPont), polyurethane, polystyrene, polycarbonate, polyacrylate, polyethylene, or polypropylene. The polymers may be reinforced with conventional reinforcing agents such as natural or synthetic fibers, e.g., nylon, or carbon black.

Figure 6:
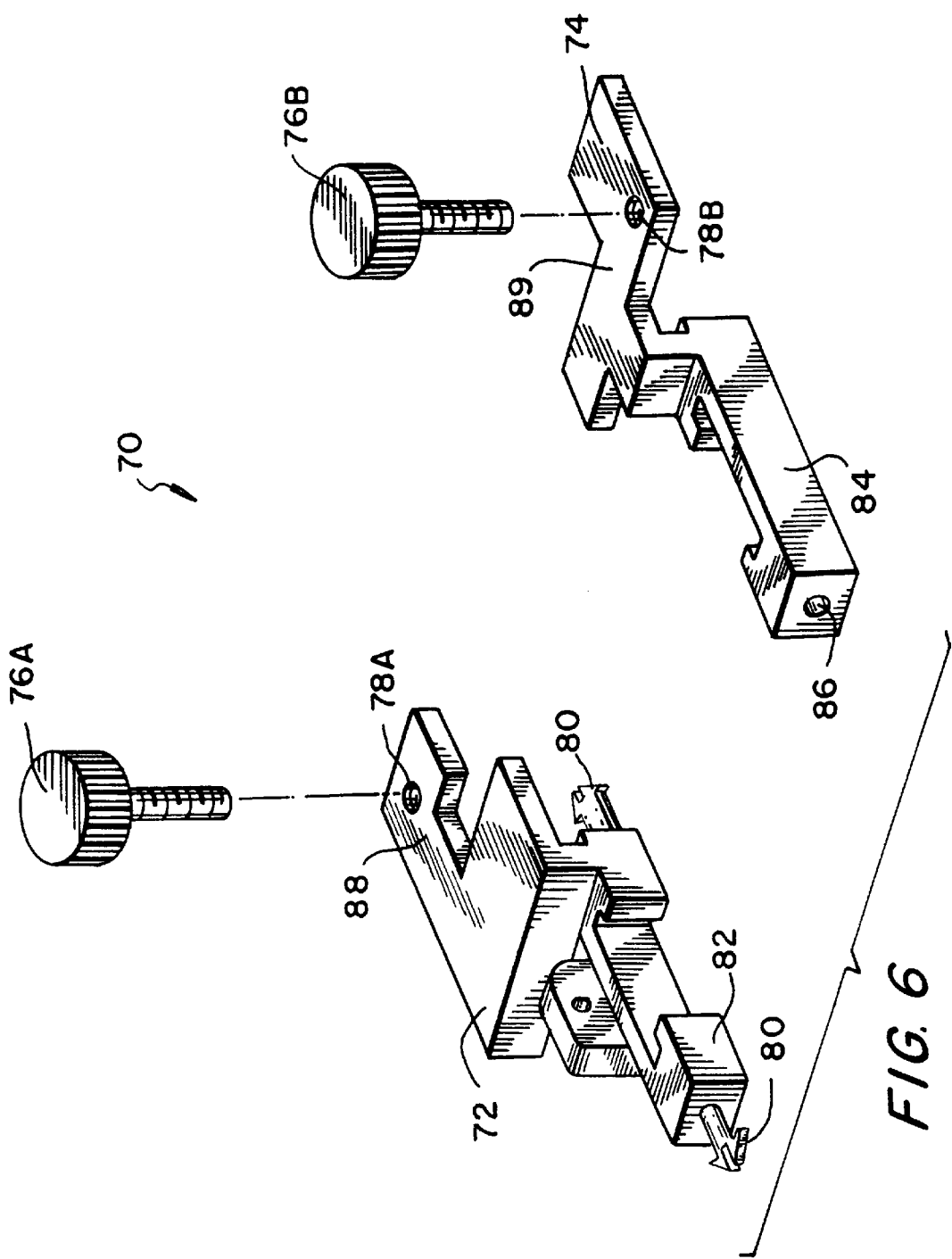
FIG. 6 is a perspective view of a swivel assembly of the embodiment of FIG. 1.

FIG. 6 shows the swivel assembly 70 in detail. Swivel assembly 70 comprises a first swivel 72 having the first blade mount 82 rotatably connected to the U-shaped rack assembly 50 opposite the rack crosspiece 58. The swivel assembly 70 also comprises a second swivel 74 having a second blade mount 84 rotatably attached to the ends of the traveler rods 24 opposite the thread assembly crosspiece 28.

The first swivel 72 comprises a first swivel arm 88, having a threaded hole 78A for passing a threaded thumbscrew 76A therethrough. An end of the threaded screw 76A contacts a surface of platform 56 extending from second leg 54. The second swivel 74 comprises a second swivel arm 89, having a threaded hole 78B for passing a threaded thumbscrew 76B therethrough. An end of the threaded screw 76B contacts the surface of platform 56 extending from second leg 54. In other embodiments, not shown, it is conceivable that the thumbscrew 76A of the first swivel assembly 72 would contact a different leg or extension of leg than would the thumbscrew 76B of the second swivel assembly 74. The heads of the thumbscrews 76A, 76B are large enough, and have a suitably grippable surface, for easy turning by a surgeon. Thus, the thumbscrews 76A, 76B typically have a diameter of about ½ inch and a knurled surface. The thumbscrews 76A, 76B are preferably plastic.

Prongs 80 (FIG. 6) of opposed sides of the first blade mount 82 are inserted into openings 60 (FIG. 5) of the rack assembly 50 to rotatably attach the first swivel 72 to the rack assembly 50. End 23 of the threaded rod 22 pushes against the second blade mount 84.

The swivel assembly 70 swivels to permit adjustment of the angle of the blades 91, 92 relative to the rack assembly 50 or thread assembly 20 to which the respective blade mounts 82, 84 are rotatably mounted.

The adjustment of the angle of the blades 91, 92 permits the blades to fan out within the patient's body such that the blade distal ends 96, 97 are further apart from each other than are the blade proximal ends 94, 95. This angle adjustment is easily accomplished by turning the thumbscrews 76A, 76B to protrude from the respective swivel arm 88, 89, the appropriate distance to force the blades 91, 92 to take the desired angle. Lower ends of the thumbscrews 76A, 76B, after sufficient turning, push against the platform 56 to cause the blades 91, 92 to be held at the appropriate angle.

Typically, the blades are 2⅜ to 2½ inches wide and 1 to 6 inches long. Generally, the blades are 4 to 5 inches long. As stated above, the blades are interchangeable and preferably made of plastic to be disposable. The blade proximal ends 94, 95 can move from a closed position wherein the blades are about 0 inches apart to an open position (see FIG. 8) wherein the blades are substantially parallel and a distance "A" of about 2–4 inches, preferably about 2–3 inches, apart. By adjusting the angles X,Y of blades 91, 92 (see FIG. 8), the distal ends 96, 97 may be each moved an additional 0 to about 4 inches apart. Thus, a total internal operating window "D" of as much as about 11 inches may be achieved. If desired only one blade 91 or 92 has its angle adjusted to achieve spans "B" or "C" of up to about 7 inches.

In a typical surgery, the surgical retractor 10 of the present invention would be employed as follows.

First, the surgeon would make an incision into the patient at the appropriate location for the particular surgery. This typically involves an incision about 3 to about 5 inches long. The blades 91, 92 of the retractor 10 would be inserted through the incision while being in a closed position during which the blades 91, 92 are substantially adjacent. Generally, the blades 91, 92 are initially parallel to each other in the closed position. Then, the knob 30 is turned counterclockwise to pull the entire thread assembly 20, second blade mount 84, and second swivel 74 (which is attached to the thread assembly 20), away from the first blade mount 82. This forces the proximal end 95 of second blade 92 to move away from the proximal end 94 of the first blade 91 a sufficient distance, e.g., about 2.5 to about 4 inches, for the surgeon to perform the surgery. Typically the distance is sufficient to insert and operate surgical instruments and permit the surgeon to view internal organs and to palpate internal organs with one or two fingers.

Then the distal ends 96, 97 may be further moved apart by independently moving either or both blades 91, 92 to an angle X, Y (see FIG. 8) of between 0° and about 45° away from normal (90°) relative to the respective rack assembly 50 and thread assembly 20.

The angle of one or both blades 91, 92 relative to the rack assembly 50 and thread assembly 20, respectively, is adjusted by appropriately turning the thumbscrews 76A, 76B.

In particular, to adjust the angle of the first blade 91, thumbscrew 76A is turned clockwise to put a greater portion of thumbscrew 76A between the first swivel arm 88 and the platform 56. This causes the first swivel 72, first blade mount 82 and first blade 91 to tilt to an angle to move distal end 96 away from distal end 97.

To adjust the angle "X" of the second blade 92, the thumbscrew 76B is turned clockwise to put a relatively greater portion of thumbscrew 76B between the second swivel arm 89 and the platform 56. This causes the second swivel 74, second blade mount 84, and the second blade 92 to tilt to an angle Y to move distal end 97 away from distal end 96.

Thus, by simply turning the thumbscrews 76A, 76B, a surgeon can achieve an operating window within the patient which is up to 8 inches larger than the operating window at the surface of the patient's skin because each of the distal ends 96, 97 can move outwardly away from each other a distance of as much as about 4 inches. This makes possible a wide variety of surgeries with only a minimal incision. However, the incision is wide enough that many surgical instruments which are similar to, or the same as, those used in conventional surgeries may be employed for such an operation. Moreover, because there is a small, yet significant incision, the surgeon can put one or two fingers into the incision to actually touch the internal organs being operated on. Also, the incision permits the surgeon to see the organs being operated on. If desired, excellent lighting provided by the fiberoptics or other acceptable internal surgical lighting gives the surgeon an excellent view of the internal operating area. If desired, a surgeon can also conveniently pass an endoscope into the incision to magnify views inside the patients body as desired.

Figure 9:
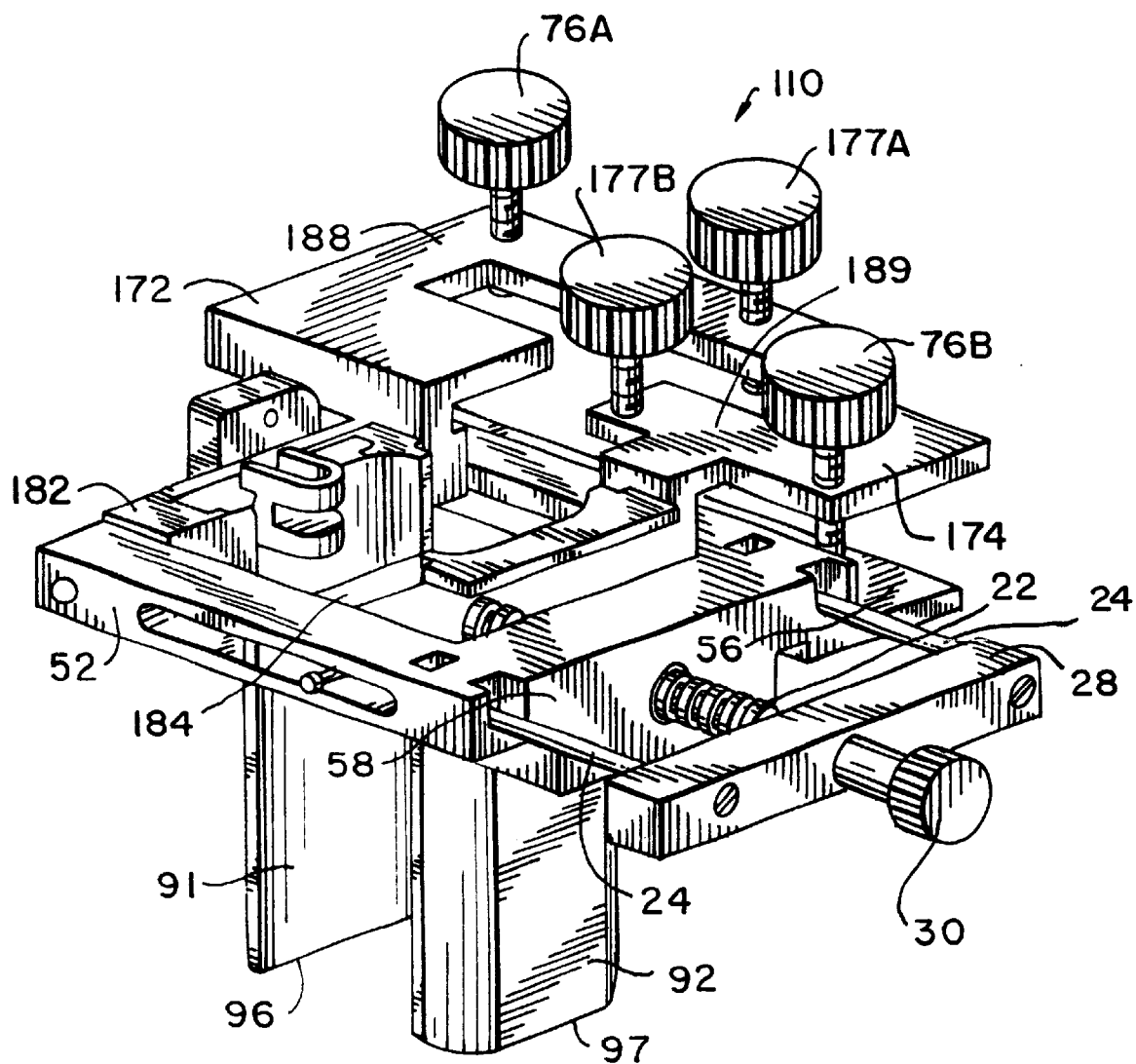
FIG. 9 is a perspective view of a second embodiment of a surgical retractor of the present invention.
Figure 10:
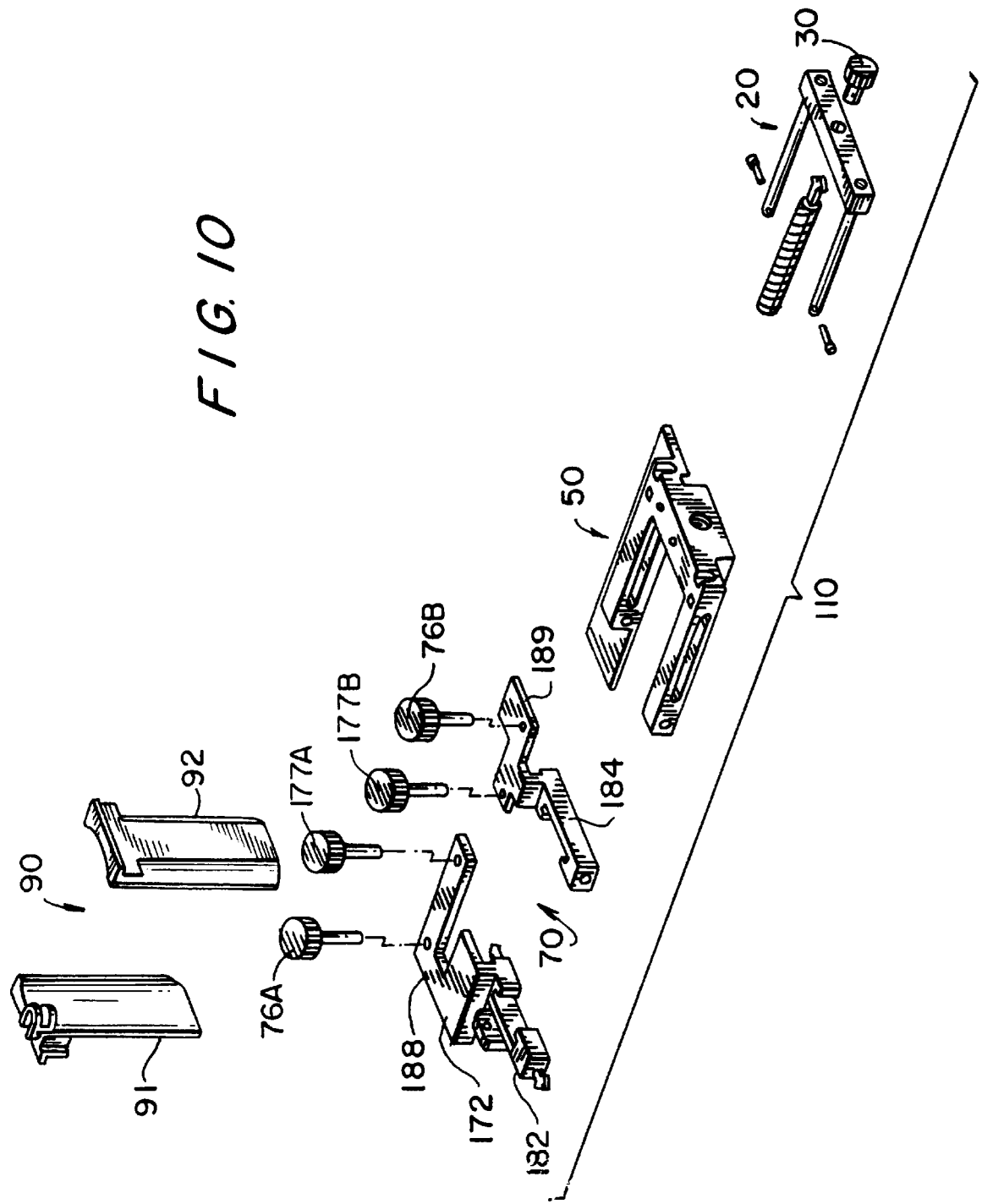
FIG. 10 is an exploded view of the embodiment of FIG. 9.

FIGS. 9 and 10 show a second embodiment of a surgical retractor 110 of the present invention. The difference between the first and second embodiments is that surgical retractor 110 has two inner thumbscrews 177A, 177B. The presence of four thumbscrews permits the blades 92, 92 to tilt outwardly or inwardly.

For the second embodiment, the angle X of the blade 91 relative to the rack assembly 50, and angle Y of the blade 92 relative to the thread assembly 20, are adjusted by appropriately turning the thumbscrews 76A, 76B, 177A, 177B.

In particular, to outwardly adjust the angle X of the first blade 91, inner thumbscrew 177A is turned counterclockwise away from platform 56. Then thumbscrew 76A is turned clockwise to put a greater portion of the thumbscrew 76A between the first platform 56 and swivel arm 188 relative to the portion of the inner thumbscrew 177A between the swivel arm 188 and the platform 56. This causes the first swivel 172, first blade mount 182 and first blade 91 to tilt to an angle to move distal end 96 away from distal end 97.

To outwardly adjust the angle Y of the second blade 92, inner thumbscrew 177B is turned counterclockwise away from platform 56. Then thumbscrew 76B is turned clockwise to put a greater portion of thumbscrew 76B between the platform 56 and second swivel arm 189 relative to the portion of the inner thumbscrew 177B between the second swivel arm 189 and the platform 56. This causes the second swivel 174, second blade mount 182 and second blade 92 to tilt to an angle to move second distal end 97 away from first distal end 96.

To inwardly adjust the blade angles, the steps for turning the thumbscrews 76A, 76B, 177A, 177B would be reversed. Namely, screws 177A, 177B would extend below their respective swivel arms 188, 189 more than would screws 76A, 76B.

FIGS. 11–16 show an actually made embodiment of the surgical retractor of the present invention. All the parts shown in white of the surgical retractor of FIGS. 11–16 are plastic. As can be seen in FIGS. 11–16, a few parts, e.g., traveling rods, screws attaching the traveling rods to the thread assembly crosspiece, pins for attaching the travelling rods to the transverse slots of the rack assembly, and a screw adjacent the knob of the thread assembly are shown to be made of metal.

Figure 11:
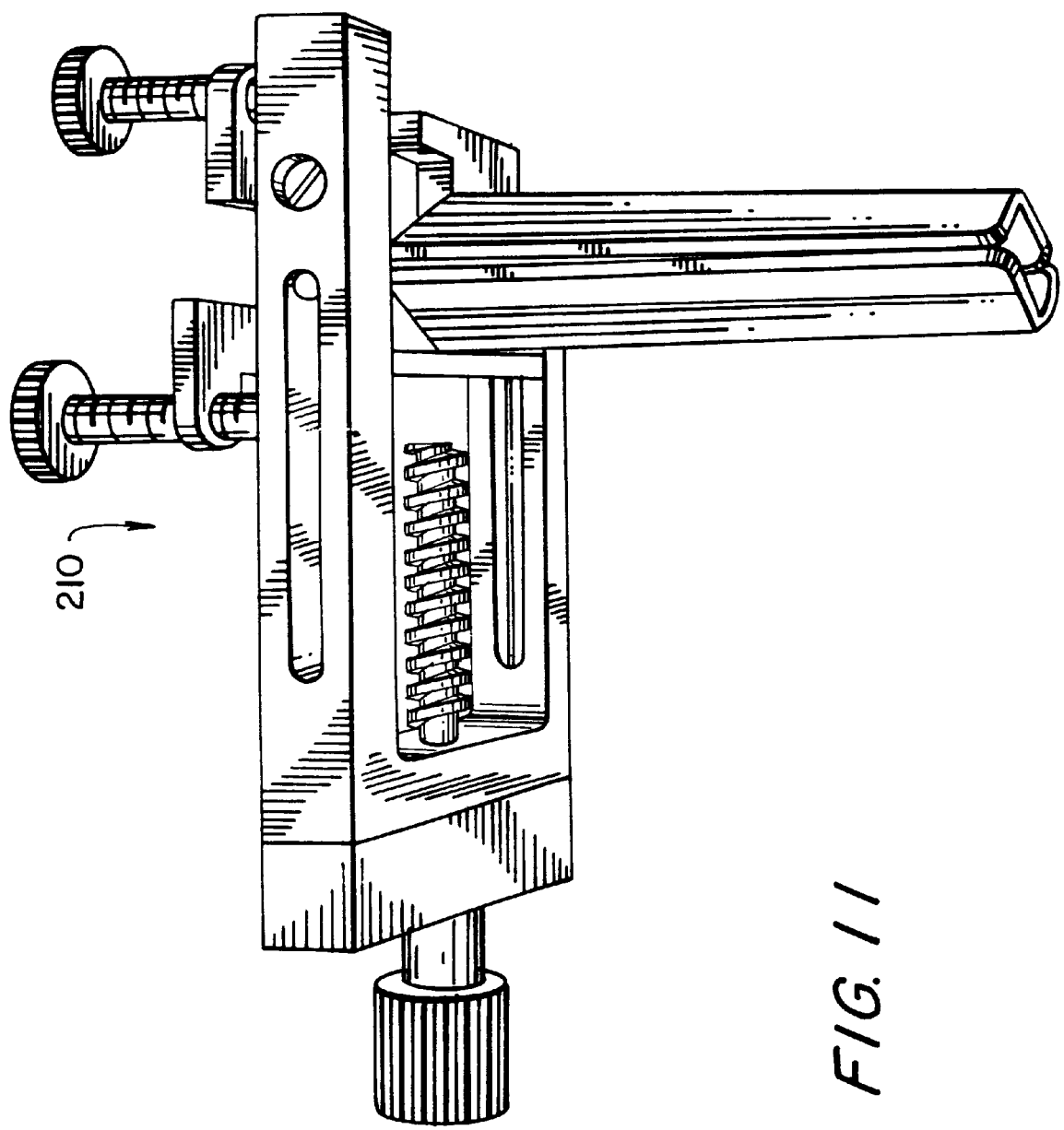
FIG. 11 is a copy of a photograph of a first view of a surgical retractor of the present invention in a closed position.

FIG. 11 is a copy of a photograph of a first view of a surgical retractor 210 of the present invention in a closed position.

Figure 12:
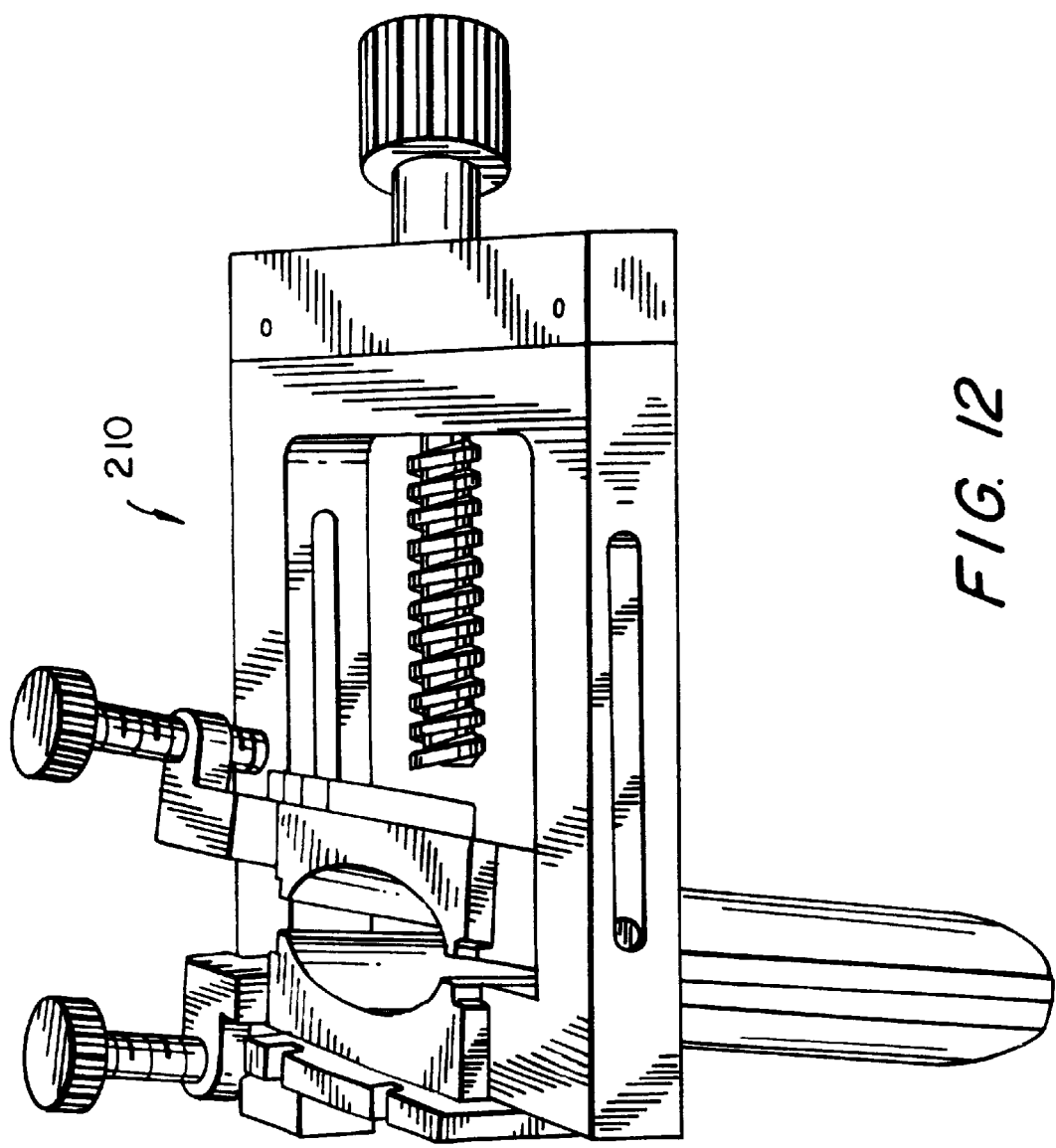
FIG. 12 is a copy of a photograph of a second view of the surgical retractor of FIG. 11 in the closed position.

FIG. 12 is a copy of a photograph of a second view of the surgical retractor 210 of FIG. 11 in the closed position.

Figure 13:
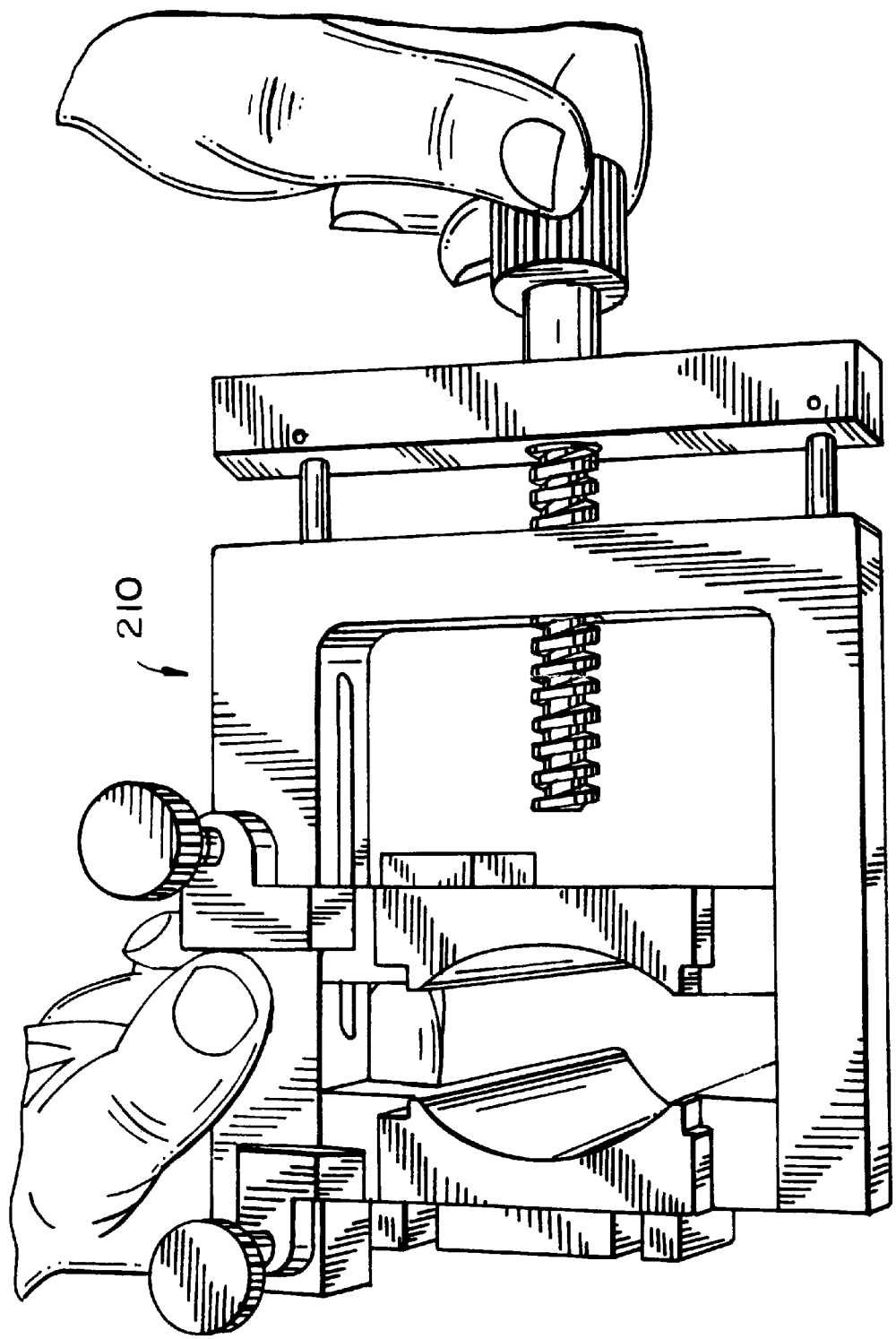
FIG. 13 is a copy of a photograph of the surgical retractor of FIG. 11 being opened.

FIG. 13 is a copy of a photograph of the surgical retractor 210 of FIG. 11 being opened.

Figure 14:
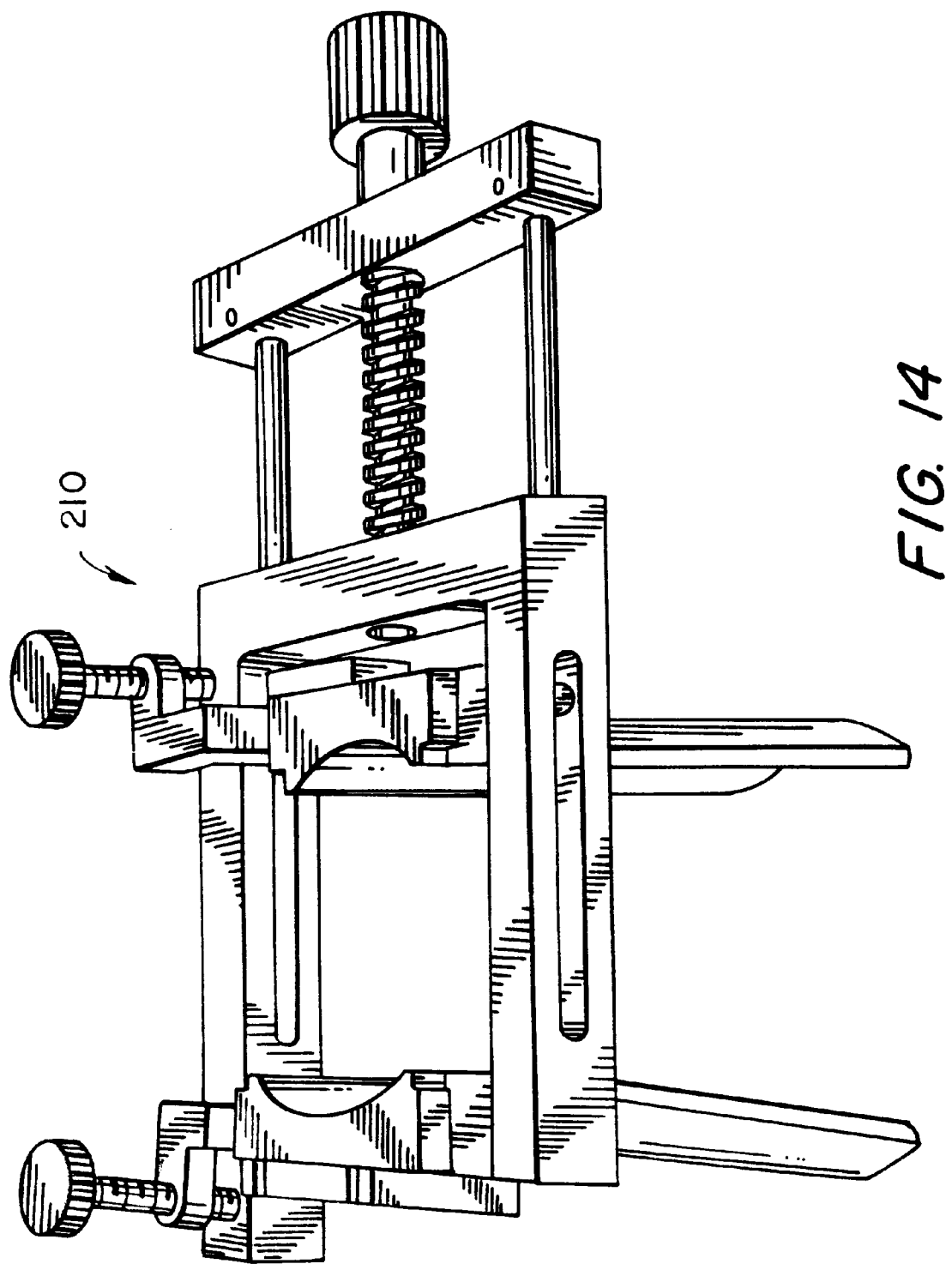
FIG. 14 is a copy of a photograph of the surgical retractor of FIG. 11 in an open position with first and second blades substantially parallel.

FIG. 14 is a copy of a photograph of the surgical retractor 210 of FIG. 11 in an open position with first and second blades substantially parallel.

Figure 15:
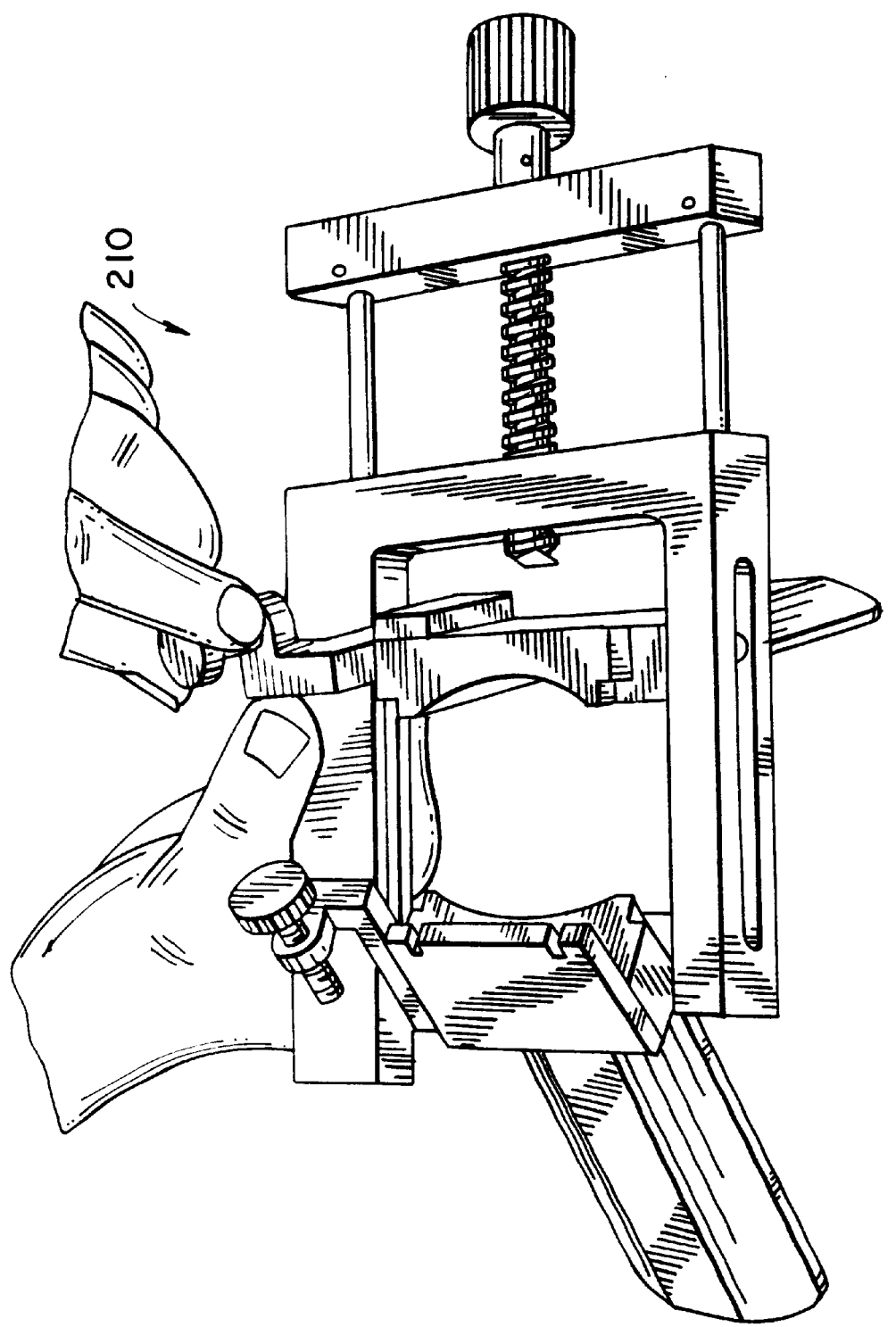
FIG. 15 is a copy of a photograph of the surgical retractor of FIG. 11 in an open position with the first blade at an acute angle and the second blade at a different angle from that of the first blade.

FIG. 15 is a copy of a photograph of the surgical retractor 210 of FIG. 11 in an open position with the first blade at a first angle and the second blade at a second angle which is different from that of the first blade.

Figure 16:
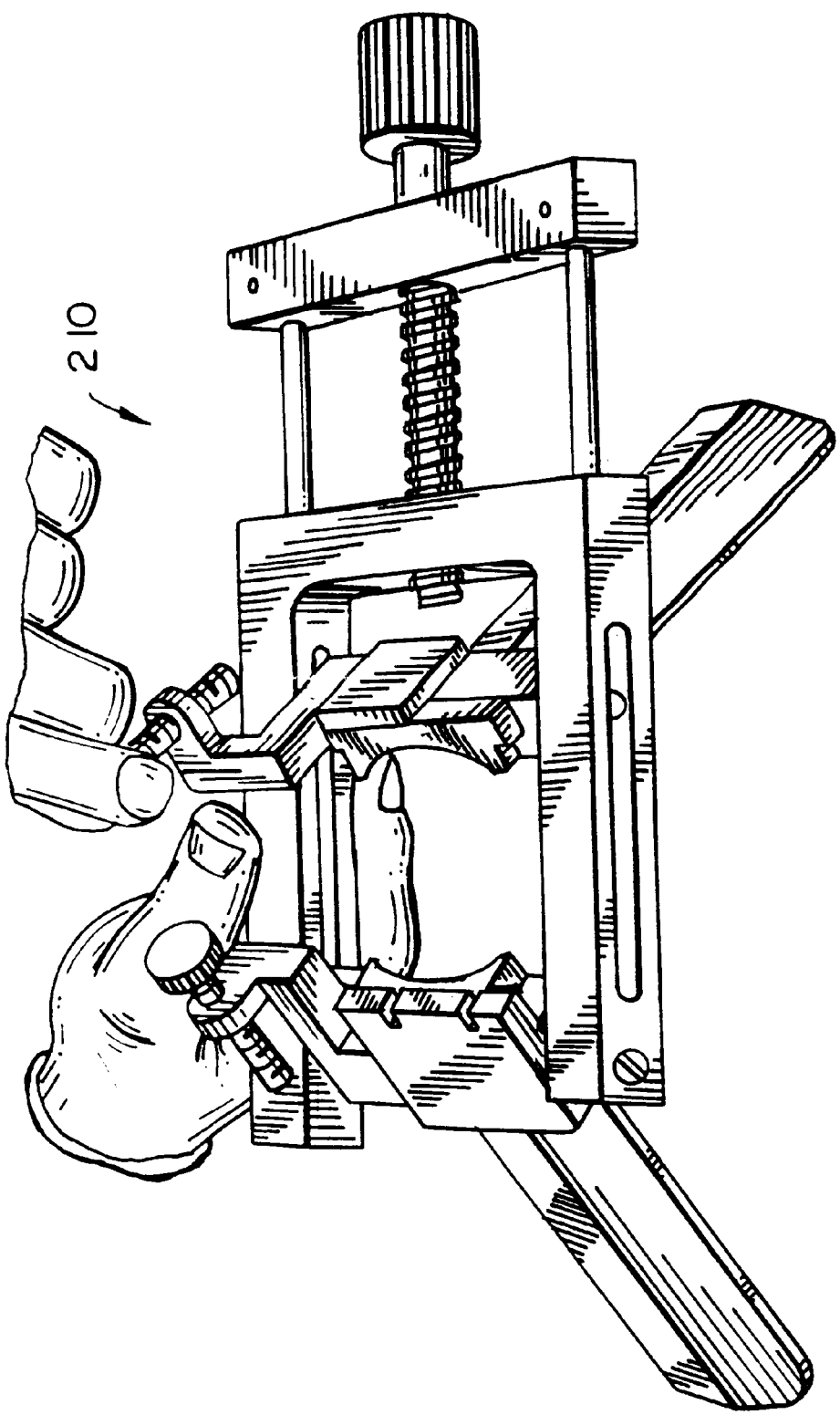
FIG. 16 is a copy of a photograph of the surgical retractor of FIG. 11 in an open position with both blades angled outwardly to form a reverse funnel.

FIG. 16 is a copy of a photograph of the surgical retractor 210 of FIG. 11 of the surgical retractor of FIG. 11 in an open position with both blades angled outwardly to form a reverse funnel.

It is also advantageous to provide the retractors of the present invention with auxiliary side blades. FIGS. 17 and 18 show front and side views, respectively, of an embodiment of such a side blade 300. The side blade 300 has a wall 302 having an inner surface 304 and an outer surface 306. The side blade 300 also has an extension 308 integral with the wall 302 and a lip 310 integral with the extension 308.

The wall 302, extension 308 and lip 310 form a U-shaped channel which snugly fits over a leg of a retractor, for example, either first leg 52 or second leg 54 of the embodiment of FIG. 5. Thus, the side blade 300 holds itself sufficiently tightly to the leg to hold back tissue in the operating field. Thus, the side blade 300 prevents caving of body organs into the operating field. This is particularly advantageous when the blades 91, 92 (FIG. 1) are positioned to have their distal ends 96, 97 (FIG. 7) a large distance apart, such as 9–11 inches apart. Of course, both first leg 52 and second leg 54 may have their own respective side blade 300. While especially advantageous when the blade distal ends 96, 97 are far apart, the side blades 300 may be used at any stage of surgery wherein the blade mounts 82, 84 are sufficiently apart for the side blade 300 to be inserted on a leg 52, 54 between the blade mounts 82, 84.

The side blade 300 typically has a thickness "T" of about 0.1 to about 0.3 inches, a length "L3" of about 1 to about 6 inches, a width "W" of about 0.75 to about 2 inches, a depth "D1" of about 0.75 to about 1.5 inches and its lip 310 has a length "L4" of about 0.5 to about 1 inch. A typical side blade 300 is about 0.16 inches thick, about 5 inches long, about 1.25 inch wide, between 0.9 and 1 inch deep and has a lip length of about 0.8 inch. The side blades 300 are interchangeable and preferably made of surgically acceptable polymer to be disposable. Typical suitable polymers are listed above with respect to blades 91, 92. The polymers may be reinforced with conventional reinforcing agents such as natural or synthetic fibers, e.g., nylon, or carbon black.

The side blade 300, if desired, may further include a thumbscrew, not shown but similar to thumbscrew 400 (FIG. 19), to pass through a hole (not shown) in an upper part of the wall 302 to contact the leg 52 or 54 to further hold the side blade 300 in place.

The side blade 300 may also be provided with a light source 320 to illuminate the operating field. Typical Light sources employ fiber optics. A preferred light source is a lightpipe having a thin lighted panel available from LUMITEX, Inc., Strongsville, Ohio. These LUMITEX panels comprise woven optical fibers. The light is emitted from the sides of the fibers through the claddings. Thus, light is provided across the panel surface. Further information regarding the lightpipes available from LUMITEX, Inc. are provided by U.S. Pat. Nos. 5,005,108, 5,618,096 and 5,613,753 incorporated herein by reference. The panels are molded into the side blade 300 or attached to the side blade 300.

In the embodiment of FIG. 17, the light source 320 is a panel of a LUMITEX lightpipe molded into the side blade 300. Light is provided through a cable 330 which passes through the wall 302 to the panel. In an alternative, not shown, a panel of LUMITEX lightpipe is attached to the side blade 300 and the cable for providing light to the panel runs over the outer surface 306 of the side blade 300.

Likewise, if desired, a LUMITEX lightpipe panel may be molded or attached to blades 91, 92 (not shown).

If desired a hand held retractor 500, such as that of FIG. 20, may be employed instead of employing the side blade 300 (or one leg may have a hand held retractor and the other leg may have a side blade). Hand held retractor 500 has a handle 510 integral with a blade 520. Preferably, the hand held retractor 500 is disposable and made of plastic. The hand held retractor 500 may also have light source 320 supplied with light cable 330 molded into the retractor 500 (FIG. 20) or attached to the retractor 500 (not shown).

It should be appreciated that many embodiments other than those specifically described above come within the spirit and scope of the present invention. Thus, the present invention is not defined by the above description, but rather, is defined by the claims appended hereto.

What is claimed is:

1. A surgical retractor apparatus comprising:
  a U-shaped rack having a first leg, a second leg and a rack crosspiece, wherein the first leg and second leg extend from respective ends of the rack crosspiece, each leg defining a respective transverse slot having open sides, the rack crosspiece defining first and second receiving holes respectively aligned with a longitudinal axis of, and in communication with, one of said transverse slots, the rack crosspiece defining a threaded opening;

a U-shaped thread assembly comprising a thread assembly crosspiece having traveler rods attached at or adjacent to opposed ends of the thread assembly crosspiece, a threaded rod rotatably attached to the thread assembly crosspiece, the threaded rod being substantially parallel to the traveler rods and located between the traveler rods, the threaded rod having opposed first and second ends, the threaded rod being connected to the rack crosspiece by the threaded opening of the rack crosspiece, each of the traveler rods slidably connected to a respective one of the legs of the rack assembly by passing through a respective one of the receiving openings into a respective one of the slots;

a first blade and a second blade, the first blade having a sidewall opposed to a sidewall of the second blade;

at least two threaded screws;

a swivel assembly comprising a first swivel and a second swivel, the first swivel has a first blade mount rotatably connected to said U-shaped rack opposite the rack crosspiece, the second swivel has a second blade mount rotatably attached to the ends of the traveler rods opposite the thread assembly crosspiece;

the first swivel comprising a first swivel arm having at least one threaded hole for passing a first screw of the at least two threaded screws therethrough, the first threaded screw contacting one of the legs of the rack to adjust an angle of the first blade relative to the legs of the rack;

the second swivel having a second arm having at least one threaded hole for passing a second screw of the at least two threaded screws therethrough, the second threaded screw contacting one of the legs of the rack to adjust an angle of the second blade relative to the legs of the rack;

wherein the blades respectively have proximal ends attached to the blade mounts and distal ends which are distal to the blade mounts.

2. The retractor of claim 1, further comprising a knob for turning the threaded rod, wherein the first end of the threaded rod contacts the second swivel and the second end of the threaded rod passes through the thread assembly crosspiece and is attached to the knob.

3. The retractor of claim 1, wherein the second leg of the rack has a platform extending from a portion of the second leg defining the respective transverse slot.

4. The retractor of claim 3, wherein the platform provides a surface of the rack which an end of at least one of the at least one threaded screws contacts.

5. The retractor of claim 4, wherein the platform is in a plane substantially parallel to a longitudinal plane of the rack crosspiece.

6. The retractor of claim 5, wherein each swivel arm has at least one of the threaded screws.

7. The retractor of claim 5, wherein all the threaded screws contact the platform.

8. The retractor of claim 1, wherein the distal ends of the blades are movable to a maximum distance apart of about 8 to about 11 inches.

9. The retractor of claim 1, wherein when the blades are in an open position such that the proximal ends of the blades are a distance apart, a distance between the blade distal ends is adjustable, by adjusting the angles of the blades, from a minimum distance to a maximum distance, wherein the maximum distance between the blade distal ends is greater than the distance between the blade proximal ends.

10. The retractor of claim 1, wherein the first blade proximal end defines a conduit for a fiberoptic cable.

11. The retractor of claim 1, wherein a respective screw passes through one of the respective slots of the respective leg and passes transversely into the respective traveler rod to slidably attach the respective traveler rod to the respective leg.

12. The apparatus of claim 1, wherein the apparatus is made of stainless steel or titanium except for the blades which are made of rigid polymer.

13. The apparatus of claim 1, wherein the U-shaped rack, U-shaped thread assembly crosspiece, first swivel, second swivel, and blades are made of rigid polymer.

14. The apparatus of claim 1, further comprising a detachable side blade which engages one of the legs of the rack.

15. The apparatus of claim 14, wherein the side blade is provided with a planar light source.

16. The apparatus of claim 14, wherein the side blade comprises a wall, an extension extending from the wall and a lip extending from the extension, the wall, extension and lip forming a U-shaped channel to engage said one of the legs of the rack.

17. A method for surgery through an incision of about 2 to about 5 inches in length comprising, providing the retractor apparatus of claim 1;

inserting the blades of the retractor into the incision;

moving the proximal ends of the blades a first distance apart, and subsequent to moving the proximal ends, moving the distal ends of the blades a second distance apart, wherein the second distance is greater than the first distance, by adjusting an angle of at least one of the respective blades relative to a longitudinal plane passing through the U-shaped rack.

* * * * *